United States Patent [19]
Essig et al.

[11] Patent Number: 5,520,703
[45] Date of Patent: May 28, 1996

[54] LAPAROSCOPIC DESCHAMP AND ASSOCIATED SUTURING TECHNIQUE

[76] Inventors: Mitchell N. Essig, 227 High Brook Ct., Pelham, N.Y. 10803; Peter J. Wilk, 185 W. End Ave., New York, N.Y. 10023

[21] Appl. No.: 73,344

[22] Filed: Jun. 7, 1993

[51] Int. Cl.$^6$ .................................................. A61B 17/04
[52] U.S. Cl. ........................................... 606/148; 606/144
[58] Field of Search .................................. 606/144–150, 606/222–227

[56] References Cited

U.S. PATENT DOCUMENTS

| | | | |
|---|---|---|---|
| 919,138 | 4/1909 | Drake et al. | 606/144 |
| 1,583,271 | 5/1926 | Biro | 606/144 |
| 3,871,379 | 3/1975 | Clarke | 606/148 |
| 4,465,070 | 8/1984 | Eguchi | 606/145 |
| 4,527,564 | 7/1985 | Eguchi et al. | 606/145 X |
| 4,923,461 | 5/1990 | Caspari et al. | 606/148 X |
| 5,147,373 | 9/1992 | Ferzli | 606/148 X |
| 5,152,769 | 10/1992 | Baber | 606/144 X |
| 5,192,287 | 3/1993 | Fournier | 606/148 X |
| 5,217,471 | 6/1993 | Burkhart | 606/148 |

Primary Examiner—Stephen C. Pellegrino
Assistant Examiner—Michael Peffley
Attorney, Agent, or Firm—R. Neil Sudol; Henry D. Coleman

[57] ABSTRACT

A laparoscopic suturing device includes an elongate shaft having a distal end and a proximal end and an arcuate tissue piercing element permanently fixed to the shaft at the distal end, the arcuate tissue piercing element lying in a plane disposed substantially transversely to the shaft. The tissue piercing element is provided at a free end, spaced from the shaft, with an eyelet, and the device has a suture thread extending through the eyelet. A distal end portion of the device is inserted through a laparoscopic trocar sleeve and the shaft of the device is turned in one direction to insert the tissue piercing element with a first end portion of the suture thread into internal tissues of the patient, a second end portion of the suture thread remaining disposed outside the patient. The first end portion of the suture thread is grasped upon insertion through the tissues and then the shaft of the suturing device is turned in the opposite direction to remove the tissue piercing element from the internal tissues. Subsequently, the suturing device and the first end portion of the suture thread are removed from the body cavity of the patient through the trocar sleeve. The end portion of the suture thread are tied to one another to form a knot outside the patient, the knot being slid back through the trocar sleeve into the body cavity of the patient.

16 Claims, 4 Drawing Sheets

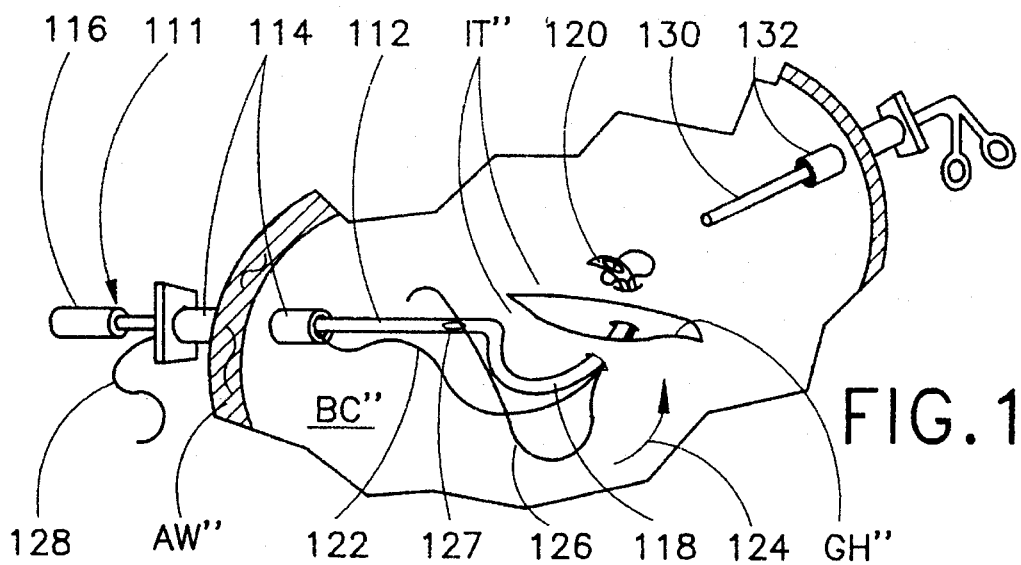
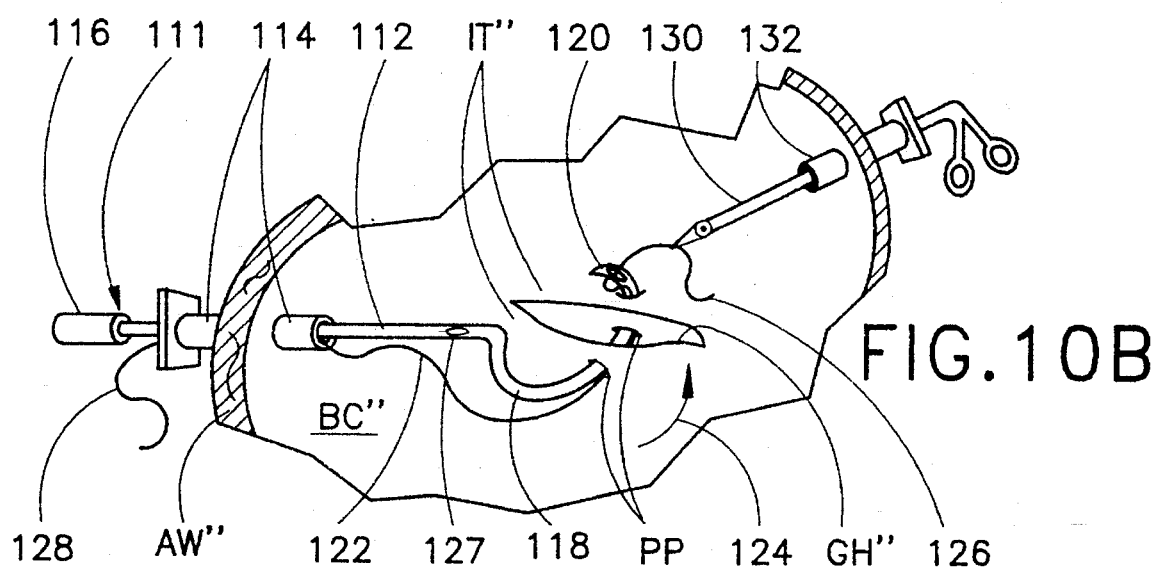
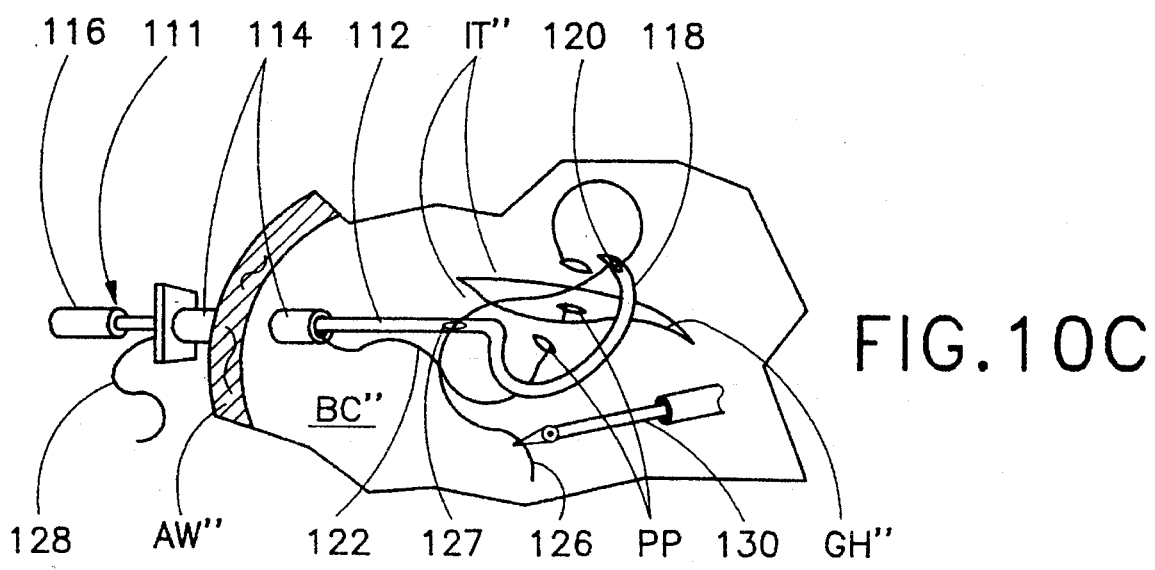

LAPAROSCOPIC DESCHAMP AND ASSOCIATED SUTURING TECHNIQUE

BACKGROUND OF THE INVENTION

This invention relates to a laparoscopic deschamp. This invention also relates to an associated suturing technique.

Laparoscopic surgery involves the insufflation of the abdominal cavity with carbon dioxide and the placement of cannulas in the abdominal wall of the patient. Distal end portions of laparoscopic instruments are inserted through the cannulas for performing an operation inside the abdominal cavity by surgeons manipulating the proximal ends of the instruments. Laparoscopic instruments include a fiber-optic laparoscope which enables visual monitoring of abdominal organs, as well as the distal end portions of the operating instruments.

Performing an operation laparoscopically, instead of via a traditional open incision, provides the substantial benefits of reducing patient trauma and hospital convalescent time. For these reasons, the number of laparoscopic surgical operations has increased enormously in the past few years. However, such operations have been generally limited to the removal of gall bladders (cholecystectomies) and various gynecological procedures. One reason for this restriction in laparoscopic applications has been the lack of a viable laparoscopic suturing method and associated instrumentation.

OBJECTS OF THE INVENTION

An object of the present invention is to provide a suturing technique for use in laparoscopic surgery.

Another object of the present invention is to provide such a technique which requires less time than conventional laparoscopic suturing techniques.

An additional object of the present invention is to provide a suturing device for use in laparoscopic surgery.

A more particular object of the present invention is to provide such a suturing device which is inexpensive.

Yet another particular object of the present invention is to provide such a suturing device which is easy to use.

These and other objects of the present invention will be apparent from the drawings and detailed descriptions herein.

SUMMARY OF THE INVENTION

A laparoscopic suturing device comprises, in accordance with the present invention, an elongate shaft having a distal end and a proximal end and an arcuate tissue piercing element permanently fixed to the shaft at the distal end. The tissue piercing element extends in a plane disposed substantially transversely to the shaft and is provided at a free end, spaced from the shaft, with an eyelet for a suture thread. In addition, a catch is provided on the shaft at the distal end thereof for enabling an entrainment of a suture thread during a laparoscopic operation, the catch being separate and distinct from the eyelet and spaced therefrom.

According to another feature of the present invention, the catch includes a movable clamping element, while the suturing device further comprises an actuator attached to the shaft in part at the proximal end thereof and connected to the clamping element for shifting the clamping element in response to manipulations by an operator. The clamping element may be pivotably attached to the shaft.

According to a further feature of the present invention, the shaft is hollow, while the suturing device also comprises a suture thread inserted through the shaft and through the eyelet. In a more specific embodiment of the invention, the tissue piercing element is also hollow, and the suture thread extends from the shaft through the tissue piercing element and out through the eyelet.

According to alternative specific features of the present invention, the catch includes a hook, a spring loaded latch, or a tapered slot in the shaft.

A method for performing a suturing procedure comprises, in accordance with the present invention, the step of (a) providing a laparoscopic suturing device including an elongate shaft having a distal end and a proximal end and an arcuate tissue piercing element permanently fixed to the shaft at the distal end, the tissue piercing element lying in a plane disposed substantially transversely to the shaft. The tissue piercing element is provided at a free end, spaced from the shaft, with an eyelet or other thread entrainment element such as a tapered slot or clamp, and the device has a suture thread extending to the entrainment element. Other steps of the method include (b) disposing a laparoscopic trocar sleeve in a patient so that a distal end portion of the sleeve projects into a body cavity of the patient, (c) inserting a distal end portion of the suturing device through the trocar sleeve and into the body cavity of the patient, and (d) turning the shaft of the suturing device in one direction to insert the tissue piercing element with a first end portion of the suture thread into internal tissues of the patient, a second end portion of the suture thread being disposed outside the patient. Additional steps of the method include (e) grasping the first end portion of the suture thread upon completion of the step of turning, (f) turning the shaft in a direction opposite the one direction to remove the tissue piercing element from the internal tissues upon grasping of the first end portion of the suture thread, (g) removing the suturing device and the first end portion of the suture thread from the body cavity of the patient through the trocar sleeve, (h) tying the first end portion and the second end portion of the suture thread to one another to form a knot outside the patient, and (i) sliding the knot back through the trocar sleeve into the body cavity of the patient.

Pursuant to another feature of the present invention, the method further comprises the step of entraining the first end portion of the suture thread to the suturing device prior to the removal of the suturing device, whereby removal of the suturing device from the body cavity of the patient effects removal of the first end portion of the suture thread.

The entrainment of the suture thread may be implemented by catching the first end portion of the suture thread at a distal end of the shaft. The shaft may be provided at a distal end with a pivotable clamp, a tapered slot, a hook, a spring latch, or other structure for facilitating the capture of the suture on the shaft. Upon such a capture, the end portion of the suture may be simply wrapped about the shaft or the catch (slot, hook, latch) by using a laparoscopic graspers.

To grasp the first end portion of the suture thread upon an insertion of the thread through internal body tissues of the patient by the arcuate tissue piercing element, a laparoscopic grasper may be used. The grasper may be inserted into the body cavity of the patient through an additional trocar sleeve. This grasper is also used to wrap the suture thread about the laparoscopic instrument shaft in preparation for removing the suture end from the patient.

Pursuant to an alternative feature of the present invention, the removal of the first end portion of the suture thread from the body cavity (e.g., the abdominal cavity) of the patient is effectuated by first extracting the suturing device from the body cavity of the patient through the trocar sleeve, subsequently inserting a distal end portion of a laparoscopic grasper through the same trocar sleeve into the body cavity of the patient, manipulating the grasper to grasp the first end portion of the suture thread, and drawing the laparoscopic grasper with the first end portion of the suture thread through the trocar sleeve.

A suturing technique in accordance with the present invention is easy and quick and enables the performance of a vast number of conventional abdominal or thoracic operations laparoscopically. A suturing device may be inexpensive and yet reliable and efficient.

BRIEF DESCRIPTION OF THE DRAWING

FIG. 10A–10C are schematic perspective views illustrating successive steps in a variation of a laparoscopic suturing method in accordance with the present invention.

DETAILED DESCRIPTION

Figure 1A:
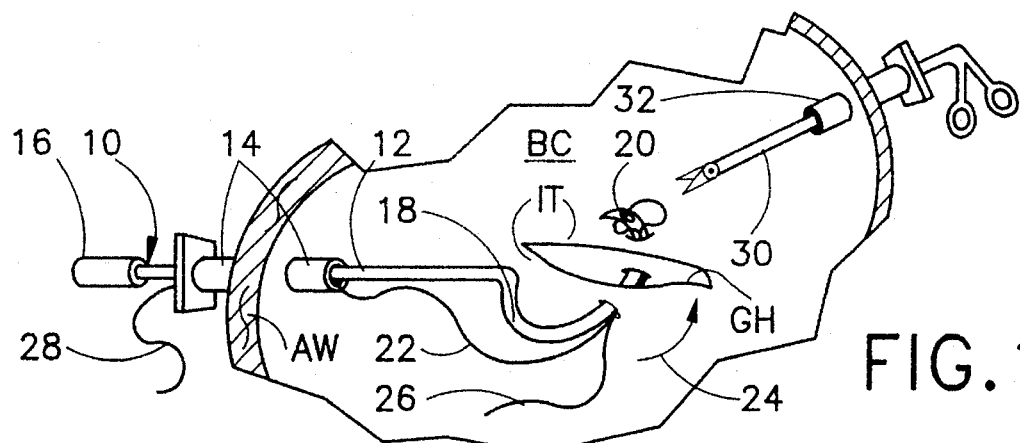
FIG. 1A is schematic perspective view of a laparoscopic suturing device partially inserted into an abdominal cavity of a patient, showing a step in a laparoscopic suturing operation in accordance with the present invention.
Figure 1B:
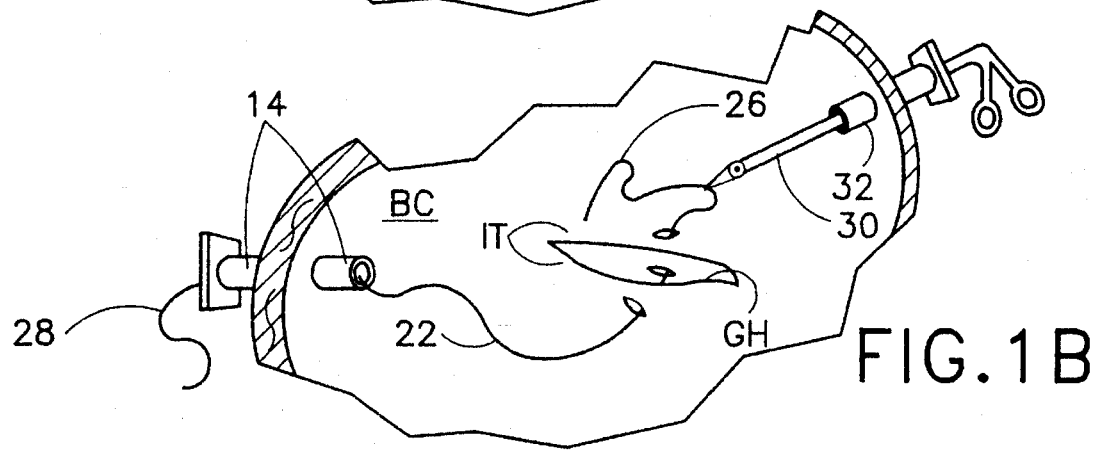
FIGS. 1B–1D are views similar to FIG. 1A, depicting subsequent successive steps in the laparoscopic suturing operation.
Figure 1C:
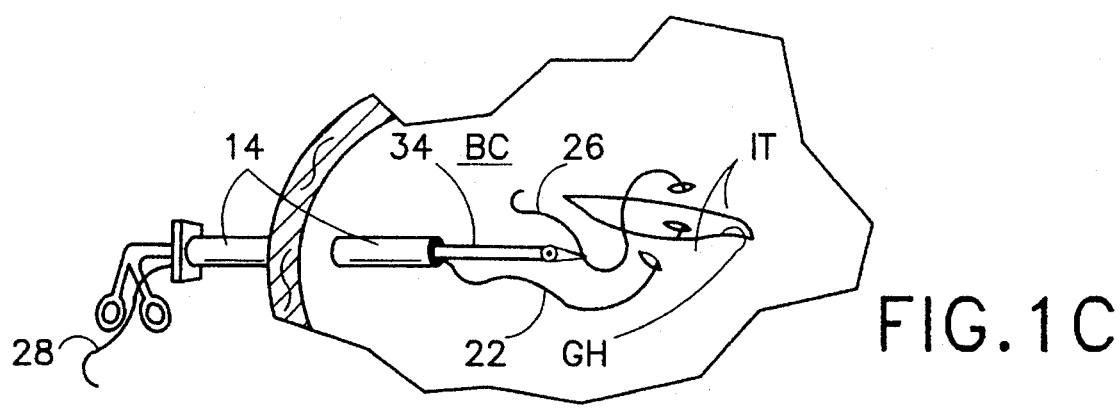

FIGS. 1A–1C illustrate the use of a laparoscopic suturing device 10 structurally similar to a deschamp of the prior art conventionally used, for example, in vaginal suturing procedures. Suturing device 10 is provided with an elongate shaft 12 long enough to be inserted through a laparoscopic trocar sleeve 14 so that a handle 16 and a proximal end of shaft 12 remain outside the patient while a distal end portion of shaft 12 is disposed in a body cavity BC of the patient such as the abdominal or thoracic cavity. Trocar sleeve 14 traverses a skin surface of the patient and is disposed, for instance, in an abdominal wall AW of the patient upon insufflation of abdominal cavity BC.

An arcuate or semicircular tissue piercing element 18 is permanently fixed to shaft 12 at the distal end thereof. Tissue piercing element 18 is sufficiently small to pass longitudinally through trocar sleeve 14 and lies in a plane disposed substantially transversely to shaft 12. Element 18 is provided at a free end, spaced from shaft 12, with an eyelet 20, through which a suture thread 22 extends. Element 18 functions similarly to a needle. However, the free end need only be so sharp as to pierce internal tissues of the patient. The sharpness of a needle, which can pierce the skin, is not required.

FIGS. 1A–1D show successive steps in the suturing of a gap or hole GH in internal tissues IT of a patient. Upon partial insertion of device 10 through trocar sleeve 14, shaft 12 is turned in a direction indicated by an arrow 24 to insert tissue piercing element 18 together with a first end portion 26 of suture thread 22 into internal tissues IT, as depicted in FIG. 1A. Suture thread 22 extends back through trocar sleeve 14 so that a second end portion 28 of suture thread 22 remains disposed outside the patient.

Upon the passing of tissue piercing element 18 and first suture end portion 26 through internal tissues IT, a laparoscopic grasper 30 inserted into abdominal cavity BC via a second trocar sleeve 32 is used to grasp suture end portion 26, as illustrated in FIG. 1B. When suture end portion 26 has been captured by grasper 30, shaft 12 is turned in a direction opposite to arrow 24 to remove tissue piercing element 18 from tissues IT. Device 10 is withdrawn from cavity BC through trocar sleeve 14.

Figure 1D:
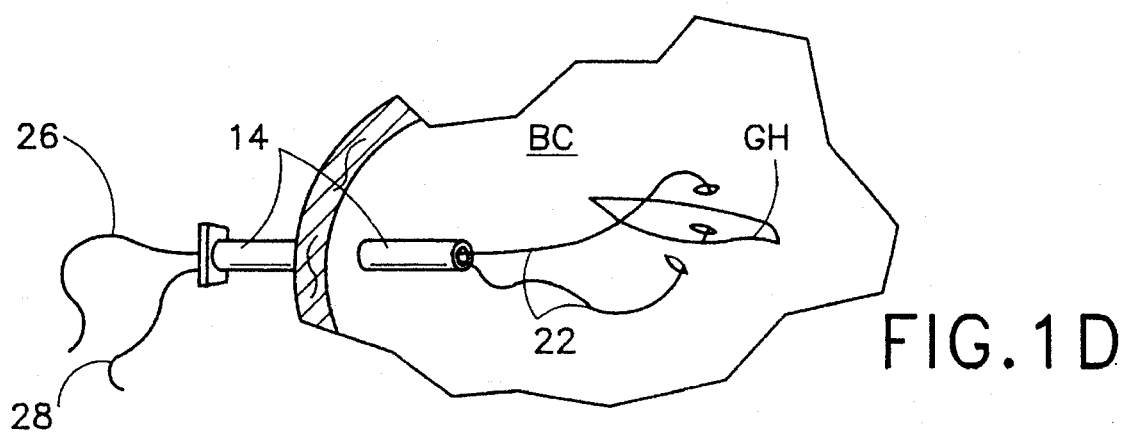

As indicated in FIG. 1C, another laparoscopic grasper 34 is then inserted through trocar sleeve 14 and used to catch suture end portion 26 as it is being held by grasper 30. Grasper 30 subsequently releases suture end portion 26, whereupon grasper 34 is withdrawn through trocar sleeve 14. At that juncture, as illustrated in FIG. 1D, both suture end portion 26 and end portion 28 are located outside the patient. The end portions are tied to one another to form a knot (not shown) which is then slid down through trocar sleeve 14 into abdominal cavity BC.

Figure 2:
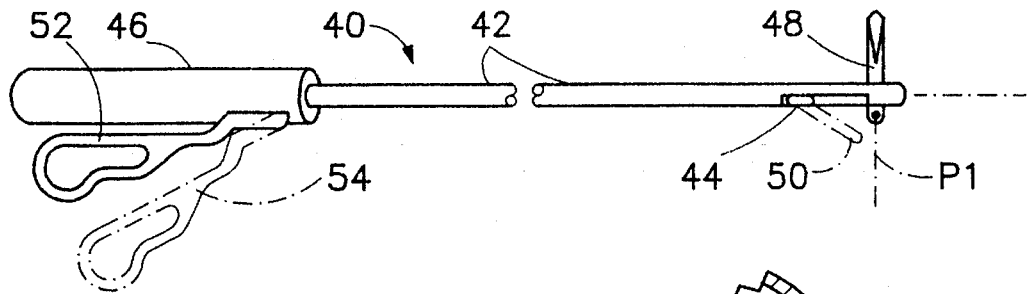
FIG. 2 is side elevational view of another laparoscopic suturing device in accordance with the present invention.

As illustrated in FIG. 2, another laparoscopic suturing device 40 comprises a shaft 42 provided at a proximal end with a handle 46 and at a distal end with an arcuate tissue piercing element 48 lying in a plane P1 oriented substantially transversely or perpendicularly with respect to shaft 42. At its distal end, shaft 42 is further provided with a clamping finger 44 pivotably attached to the shaft for alternately rotating between a closed position indicated in solid lines and an opened position indicated in dot-dash lines 50. Clamping finger 44 is operatively connected via a tensile element (not shown) to an actuator lever 52 pivotably attached to handle 46 for swinging between a clamp-closed position (solid lines) and a clamp opened position (dot-dash lines 54.

Figure 3A:
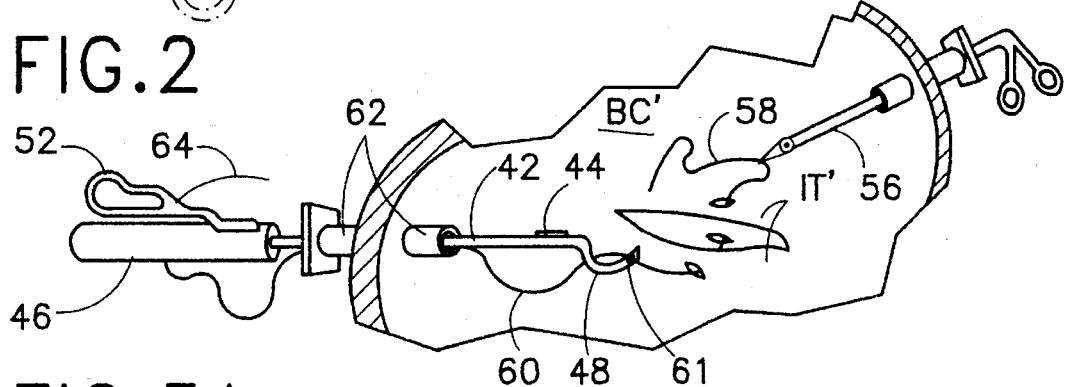
FIGS. 3A–3D are schematic partial perspective views of a patient's abdominal cavity during a laparoscopic suturing operation utilizing the device of FIG. 2, in accordance with the present invention.

FIGS. 3A–3D illustrate successive steps in the use of the device of FIG. 2. FIG. 3A shows device 40 after shaft 42 has been counterrotated to remove tissue piercing element 48 from internal tissues IT' of a patient subsequently to the operation of a grasping forceps 56 to grasp an end portion 58 of a suture thread 60 inserted through tissues IT' by element 48. Suture thread 60 extends through an eyelet 61 in tissue piercing element 48 and back out through a laparoscopic trocar sleeve 62 so that another end portion 64 of the thread is located outside the patient. Clamping finger 44 is in the closed position.

Figure 3B:
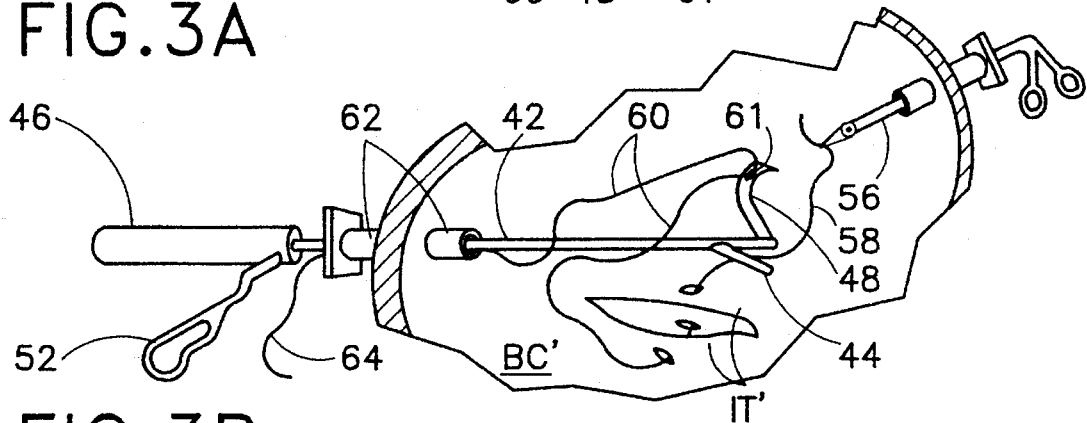

Upon the turning of shaft 42 to remove tissue piercing element 48 from the patient's internal tissues IT', laparoscopic suturing device 40 is pushed in the distal direction and actuator lever 52 is operated to open clamping finger 44, as shown in FIG. 3B. Device 40 is manipulated from outside the patient so as to insert a piece of suture end portion 58 between jaws formed by clamping finger 44 and shaft 42. Actuator lever 52 is then operated to close clamping finger 4.4 against shaft 42 and to thereby catch suture end portion 58.

Figure 3C:
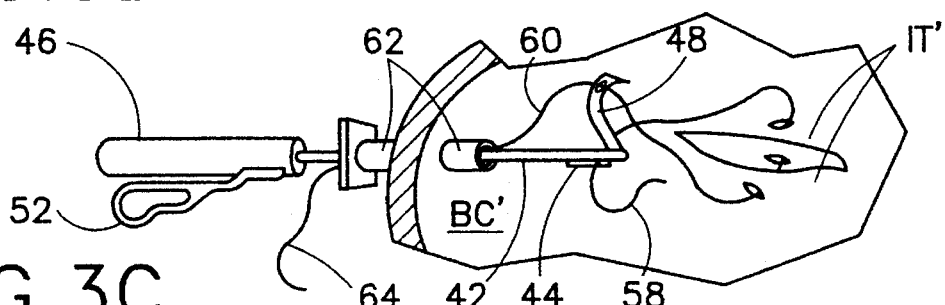
Figure 3D:
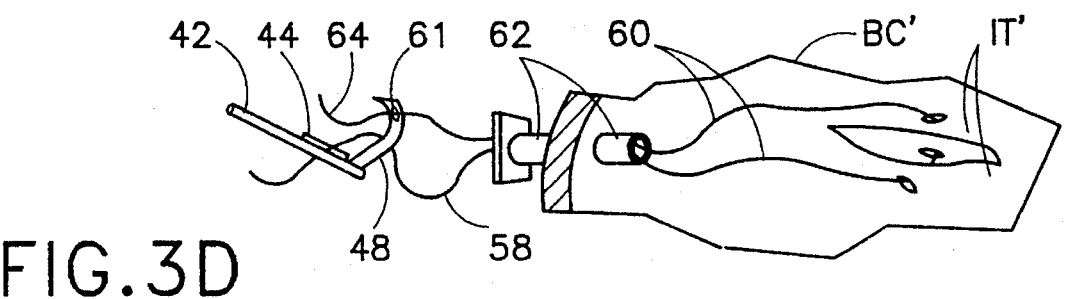

Upon the capture of suture end portion 58, as depicted in FIG. 3C, laparoscopic suturing device 40 is withdrawn from a body cavity BC' into which it has been partially inserted via trocar sleeve 62. Because suture end portion 58 is entrained by clamping finger 44, that suture end portion is also drawn outside the patient, as illustrated in FIG. 3D. Suture end portions 58 and 64 are then tied to one another to form a knot (not shown) which is then slid down through trocar sleeve 62 into body cavity BC'.

Figure 4:
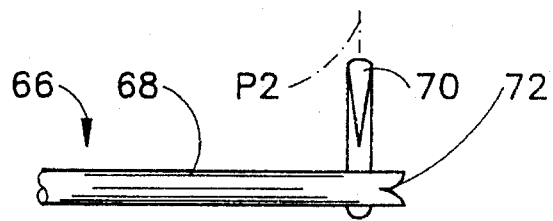
FIG. 4 is a partial schematic side elevational view of another laparoscopic suturing device in accordance with the present invention.

As illustrated in FIG. 4, a further laparoscopic suturing device 66 comprises a shaft 68 provided at a distal end with an arcuate tissue piercing element 70 lying in a plane P2 oriented substantially transversely or perpendicularly with respect to shaft 68. At its distal tip, shaft 68 is further provided with a tapered slot 72 for receiving and catching a suture thread end portion (not illustrated) upon a turning of shaft 68 to withdraw tissue piercing element 70 from a patient's internal tissues. Device 66 is shifted in the distal direction towards a suture distal end portion held by a grasping forceps (e.g., 56 in FIGS. 3A and 3B). Upon a sliding of the suture thread into slot 72, grasping forceps 56 is used to wrap the distal end portion of the suture about the distal end of shaft 68, thereby forming a friction lock enabling the entrainment and removal of the suture thread portion upon a withdrawal of device 66.

Figure 5:
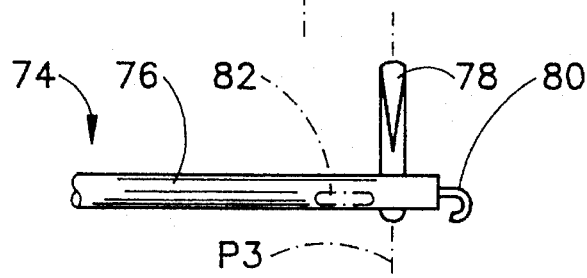
FIG. 5 is a partial schematic side elevational view of a further laparoscopic suturing device in accordance with the present invention.

As depicted in FIG. 5, a laparoscopic suturing device 74 includes a shaft 76 provided at a distal end with a tissue piercing element 78 lying in a plane P3 oriented substantially transversely or orthogonally with respect to shaft 76. At its distal tip, shaft 76 carries a hook 80 for receiving and catching a suture thread end portion (not illustrated) upon a withdrawal of tissue piercing element 78 from a patient's internal tissues. Device 74 is translated distally towards a suture distal end portion held by a grasping forceps (e.g., 56 in FIGS. 3A and 3B). Upon a sliding of the suture thread into hook 80, grasping forceps 56 is used to wrap the distal end portion of the suture about the distal end of shaft 68, thereby forming a friction lock enabling the entrainment and removal of the suture thread portion upon a withdrawal of device 74. Neither slot 72 nor hook 80 need be located at the distal tip of the respective instrument shaft 68 and 76. Instead, as indicated at 82 in FIG. 5, hook 80 may be spaced from the distal end of shaft 76.

Figure 6:
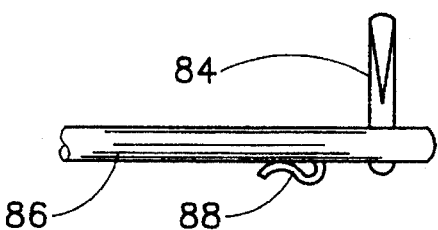
FIG. 6 is a partial schematic side elevational view of yet another laparoscopic suturing device in accordance with the present invention.

FIG. 6 shows yet another embodiment of a suturing device utilizable in laparoscopic surgery to close a wound, recess or hole in a patient's internal organs. A shaft 86 carries an arcuate, i.e., substantially semicircular, tissue piercing element 84 at a distal end. A leaf spring 88 is attached to shaft 86 near element 84 for use in catching a suture thread as described above with respect to FIGS. 4 and 5.

It is to be noted that the distal end of shaft 68, 76, or 86 may be resting on an internal organ of the patient during the wrapping of a suture thread portion about the distal end of shaft 68, hook 80, or spring clip 88, respectively. This resting of the instrument assembly steadies the instrument and facilitates the entrainment of the distal end portion of the suture thread to the instrument.

Figure 7:
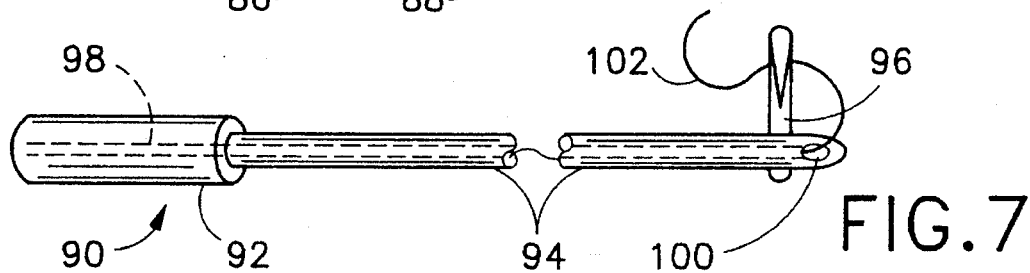
FIG. 7 is a partial schematic side elevational view of an additional laparoscopic suturing device in accordance with the present invention.

As illustrated in FIG. 7, a laparoscopic suturing device 90 having a handle 92, a shaft 94 and arcuate tissue piercing element 96 is provided with a channel 98 extending longitudinally through the handle and the shaft to an aperture 100 at the distal tip of shaft 94. A suture thread 102 has a sufficient degree of rigidity to enable insertion of the thread through channel 98 from the proximal end of handle 92. Suture thread 102 emerges from aperture 100 and is inserted through an eyelet (not shown) at the free end of element 96.

Figure 8:
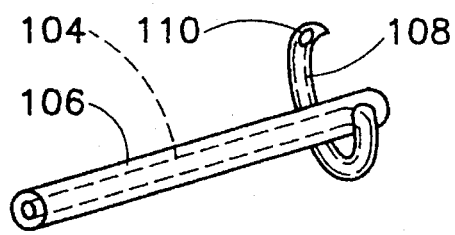
FIG. 8 is a partial schematic perspective view of a modified laparoscopic suturing device in accordance with the present invention.
Figure 9:
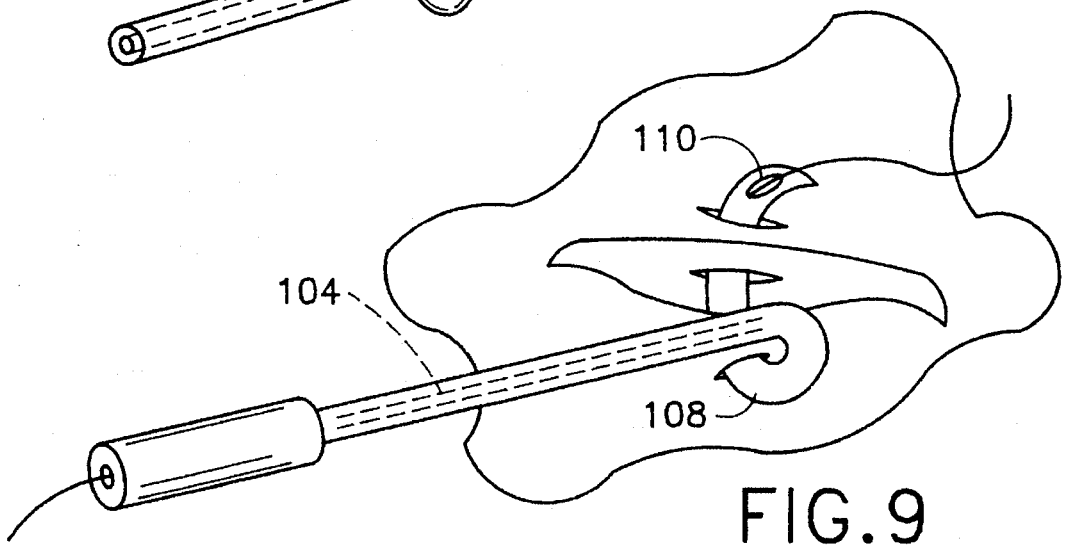
FIG. 9 is a partial schematic perspective view of the laparoscopic suturing device of FIG. 8, showing a step in the use of the instrument.

As shown in FIGS. 8 and 9, in a variation of the laparoscopic suturing device of FIG. 7, a suture guide channel 104 extends through an instrument shaft 106 and through an arcuate tissue piercing element 108 to emerge from an eyelet 110 at the free end of the tissue piercing element. As shown in FIG. 9 the laparoscopic suturing devices of FIGS. 7 and 8 provide the advantage of removing a portion of the suture thread from the surgical site, thereby facilitating the perception and handling of the distal end portion of the thread during suturing operations.

FIGS. 10A–10C illustrate the use of another laparoscopic suturing device 111. Suturing device 111 is provided with an elongate shaft 112 long enough to be inserted through a laparoscopic trocar sleeve 114 so that a handle 116 and a proximal end of shaft 112 remain outside the patient while a distal end portion of shaft 112 is disposed in a body cavity BC" of the patient such as the abdominal or thoracic cavity. Trocar sleeve 114 traverses a skin surface of the patient and is disposed, for instance, in an abdominal wall AW" of the patient upon insufflation of abdominal cavity BC".

An arcuate or semicircular tissue piercing element 118 is permanently fixed to shaft 112 at the distal end thereof Tissue piercing element 118 is sufficiently small to pass longitudinally through trocar sleeve 114 and lies in a plane disposed substantially transversely to shaft 112. Element 118 is provided at a free end, spaced from shaft 112, with an eyelet 120, through which a suture thread 122 extends. The free end of element 118 is sufficiently sharp to pierce internal tissues of the patient.

Upon partial insertion of device 111 through trocar sleeve 114, shaft 112 is turned in a direction indicated by an arrow 124 to insert tissue piercing element 118 together with a first end portion 126 of suture thread 122 into internal tissues IT" as depicted in FIG. 10A The distal end of shaft 112 is provided with a catch 127 such as spring clip 88 (FIG. 6) or tapered slot 72 (FIG. 4) whereby a short distal end portion 126 of suture thread 122 is entrained during the insertion of tissue piercing element 118 through tissues IT" as depicted in FIG. 10A. Suture thread 122 extends back through trocar sleeve 114 so that a second end portion 128 of suture thread 122 remains disposed outside the patient.

Upon the passing of tissue piercing element 118 and first suture end portion 126 through internal tissues IT", a laparoscopic grasper 130 inserted into abdominal cavity BC" via a second trocar sleeve 132 is used to grasp suture end portion 126, as illustrated in FIG. 10B. When suture end portion 126 has been captured by grasper 130, shaft 112 is turned in a direction opposite to arrow 124 to remove tissue piercing element 118 from tissues IT". Grasper 130 is then manipulated to reinsert suture end portion 126 in catch 127. Subsequently, upon a withdrawing of instrument 111 back out through trocar sleeve 114, suture thread slips through perforations PP made in tissues IT" and suture end portion 126 is brought outside the patient for knotting with end portion 128.

The procedure of FIGS. 10A–10C is believed to facilitate the suturing process by minimizing the length of suture end portion 126 prior to the operation of graspers 130. Suture thread portion 126 is easy to identify owing to its free end being located near the distal end of shaft 112.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A laparoscopic suturing device comprising:

an elongate shaft having a distal end and a proximal end;

an arcuate tissue piercing element permanently fixed to said shaft at said distal end, said tissue piercing element lying in a plane disposed substantially transversely to said shaft, said tissue piercing element being provided at a free end, spaced from said shaft, with an eyelet for a suture thread; and catch means on said shaft at said distal end thereof for enabling an entrainment of a suture thread, said catch means being separate and distinct from said eyelet and spaced therefrom.

2. The device defined in claim 1 wherein said catch means includes a movable clamping element, further comprising actuator means attached to said shaft in part at said proximal end thereof and connected to said clamping element for shifting same in response to manipulations by an operator.

3. The device defined in claim 2 wherein said clamping element is pivotably attached to said shaft.

4. The device defined in claim 1 wherein said shaft is hollow, further comprising a suture thread inserted through said shaft and through said eyelet.

5. The device defined in claim 4 wherein said tissue piercing element is also hollow, said suture thread extending from said shaft through said tissue piercing element and out through said eyelet.

6. The device defined in claim 1 wherein said catch means includes a hook.

7. The device defined in claim 1 wherein said catch means includes a spring loaded latch.

8. The device defined in claim 1 wherein said catch means includes a tapered slot in said shaft.

9. A method for performing a suturing procedure, comprising the steps of:

providing a laparoscopic trocar sleeve and a laparoscopic suturing device, said suturing device including an elongate shaft having a distal end and a proximal end and an arcuate tissue piercing element permanently fixed to said shaft at said distal end, said tissue piercing element lying in a plane disposed substantially transversely to said shaft, said tissue piercing element being provided at a free end, spaced from said shaft, with entrainment means for entraining a suture thread, said device having a suture thread extending to said entrainment means;

disposing said laparoscopic trocar sleeve in a patient so that a distal end portion of said sleeve projects into a body cavity of the patient;

inserting a distal end portion of said suturing device through said trocar sleeve and into the body cavity of the patient;

turning said shaft in one direction to insert said tissue piercing element with a first end portion of said suture thread into internal tissues of the patient, a second end portion of said suture thread being disposed outside the patient;

upon completion of said step of turning, grasping said first end portion of said suture thread;

upon grasping of said first end portion of said suture thread, turning said shaft in a direction opposite said one direction to remove said tissue piercing element from said internal tissues;

removing said suturing device and said first end portion of said suture thread from the body cavity of the patient through said trocar sleeve;

tying said first end portion and said second end portion of said suture thread to one another to form a knot outside the patient; and sliding said knot back through said trocar sleeve into the body cavity of the patient.

10. The method defined in claim 9, further comprising the step of entraining said first end portion of said suture thread to said suturing device prior to said step of removing, whereby removal of said suturing device from the body cavity of the patient effects removal of said first end portion of said suture thread.

11. The method defined in claim 10 wherein said step of entraining includes the step of catching said first end portion of said suture thread on said suturing device.

12. The method defined in claim 11 wherein said step of catching includes the step of wrapping said first end portion of said suture thread around a part of said suturing device.

13. The method defined in claim 12 wherein said step of wrapping includes the step of manipulating a laparoscopic graspers to wrap said first end portion of said suture thread around said part of said suturing device.

14. The method defined in claim 11 wherein said step of catching includes the step of inserting said first end portion of said suture thread into a clamping member on said shaft.

15. The method defined in claim 9 wherein said step of removing includes the steps of:

first extracting said suturing device from the body cavity of the patient through said trocar sleeve;

subsequently inserting a distal end portion of a laparoscopic grasper through said trocar sleeve into the body cavity of the patient;

manipulating said grasper to grasp said first end portion of said suture thread; and drawing said laparoscopic grasper with said first end portion of said suture thread through said trocar sleeve.

16. A method of performing a suturing procedure, comprising the steps of:

providing a laparoscopic trocar sleeve and a laparoscopic suturing device, said suturing device including an elongate shaft having a distal end and a proximal end and an arcuate tissue piercing element permanently fixed to said shaft at said distal end, said tissue piercing element lying in a plane disposed substantially transversely to said shaft, said tissue piercing element being provided at a free end, spaced from said shaft, with entrainment means for entraining a suture thread, said device having a suture thread extending to said entrainment means;

disposing said laparoscopic trocar sleeve in a patient so that a distal end portion of said sleeve projects into a body cavity of the patient;

inserting a distal end portion of said suturing device through said trocar sleeve and into the body cavity of the patient;

turning said shaft in one direction to insert said tissue piercing element with a first end portion of said suture thread into internal tissues of the patient, a second end portion of said suture thread being disposed outside the patient;

inserting a distal end portion of a laparoscopic grasper through an additional trocar sleeve into the body cavity of the patient;

upon completion of said step of turning, manipulating said grasper to grasp said first end portion of said suture thread;

upon grasping of said first end portion of said suture thread, turning said shaft in a direction opposite said one direction to remove said tissue piercing element from said internal tissues;

removing said suturing device and said first end portion of said suture thread from the body cavity of the patient through said trocar sleeve;

tying said first end portion and said second end portion of said suture thread to one another to form a knot outside the patient; and sliding said knot back through said trocar sleeve into the body cavity of the patient.

* * * * *